United States Patent [19]

Krüger et al.

[11] Patent Number: 5,238,907
[45] Date of Patent: Aug. 24, 1993

[54] SUBSTITUTED 2-PYRIMIDINYL-ACETIC ACID DERIVATIVES, AND THEIR USE AS HERBICIDES, FUNGICIDES AND PLANT GROWTH REGULATORS

[75] Inventors: Gabriele Krüger; Christoph Harde; Nikolaus Heinrich; Anita Krüger; Erhard Nordhoff; Gerhard Tarara; Peter Wegner; Clemens Kötter; Gerhard Johann; Richard Rees, all of Berlin, Fed. Rep. of Germany; Graham P. Jones, Sawston, England

[73] Assignee: Schering Aktiengesellschaft, Fed. Rep. of Germany

[21] Appl. No.: 818,518

[22] Filed: Jan. 9, 1992

Related U.S. Application Data

[62] Division of Ser. No. 590,675, Oct. 1, 1990, Pat. No. 5,098,465.

[30] Foreign Application Priority Data

Oct. 9, 1989 [DE] Fed. Rep. of Germany ....... 3934020

[51] Int. Cl.$^5$ .................. C07D 239/52; C07D 239/47; C07D 239/48; A01N 43/54
[52] U.S. Cl. ..................... 504/239; 504/242; 504/243; 544/335; 544/334; 544/326; 544/327; 544/329; 544/319; 544/242
[58] Field of Search ............ 71/92; 544/335, 334, 544/326, 327, 329, 319, 242; 504/239, 242, 243

[56] References Cited

FOREIGN PATENT DOCUMENTS 7509M 12/1969 France .

OTHER PUBLICATIONS

Sane et al., Chemical Abstracts, vol. 83, entry 79200k (1975).
Brown et al., Chemical Abstracts, vol. 87, entry 23201 b (1977).
Brown et al., Chemical Abstracts, vol. 89, entry 23539j (1978).
Niitsuma et al., vol. 91, entry 5189g (1979) Chemical Abstracts.
Sakamoto et al., Chemical Abstracts, vol. 94 entry 156852f (1981).
Journal of The Chemical Society Perkin Trans. I. (1987), Seiten 2523-2529, London, GB; T. Nishio et al.: "Photochemical reactions of pyrimidinethiones with alkenes".
Chemical Abstracts, Band 83, (1975), Seite 661, Zusammenfassung Nr. 79200k, Columbus, Ohio, US; R. T. Sane et al., "Synthesis of new copper(II) complexes of the derivatives of 2,4,6-trichloro-s-triazine", & Curr. Sci. 1975, 44(7), 220–1.
Chemical Abstracts, Band 91, (1979), Seite 659, Zusammenfassung Nr. 175289g, Columbus, Ohio, US; H. Yamanaka et al.: "Studies on pyrimidine derivatives. XI. Reaction of ethoxycarbonylacetamidine with beta-dicarbonyl compounds" and Yakugaku Zasshi 1979, 99(4), 342–8.

Primary Examiner—John M. Ford
Attorney, Agent, or Firm—Ostrolenk, Faber, Gerb & Soffen

[57] ABSTRACT

The invention relates to new 2-pyrimidinyl- and 2-triazinylacetic acid derivatives of general formula I

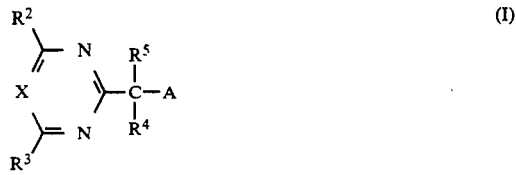

(I)

in which A, $R^{2-5}$ and X have the meanings given in the description, processes for their preparation and their use as herbicides, fungicides and plant growth regulants.

17 Claims, No Drawings

SUBSTITUTED 2-PYRIMIDINYL-ACETIC ACID DERIVATIVES, AND THEIR USE AS HERBICIDES, FUNGICIDES AND PLANT GROWTH REGULATORS

This is division of application Ser. No. 07/590,675, filed Oct. 1, 1990, and now U.S. Pat. No. 5,098,465.

This invention relates to new substituted 2-pyrimidinyl- and 2-triazinylacetic acid derivatives, processes for their preparation and their use as herbicides, fungicides and plant growth regulators.

It is known that pyrimidine derivatives possess herbicidal activity (EP 223 406, 249 707, 249 708, 287 072 and 287 079). However, the herbicidal activity of these known compounds is often insufficient or selectivity problems are seen in important crops.

The object of the present invention is to make new compounds that do not have these disadvantages and have improved biological properties over the known compounds.

It has now been found that substituted 2-pyrimidinyl- and 2-triazinylacetic acid derivatives of general formula I

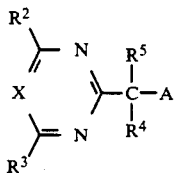

in which
A is one of the groups $-CO-OR^1$, $-CO-NR^6R^7$ or $-C\equiv N$,
$R^1$ is hydrogen, $C_1$-$C_{12}$-alkyl (optionally substituted by hydroxy, halogen, $C_1$-$C_4$-alkoxy, $C_1$-$C_4$-alkylthio, $C_3$-$C_6$-cycloalkyl, benzyl, furyl, tetrahydrofuryl, phenyl, halophenyl, $C_1$-$C_4$-alkylphenyl, $C_1$-$C_4$-alkoxyphenyl, nitrophenyl, cyano, carboxy, $C_1$-$C_4$-alkoxycarbonyl, $C_1$-$C_4$-alkylamino, di-$C_1$-$C_4$-alkylamino, tri-$C_1$-$C_4$-alkylammoniumhalide, $C_2$-$C_5$-alkylenimino or di-$C_1$-$C_4$-alkylmethyleniminooxy), $C_2$-$C_{12}$-alkyl, interrupted by one or more oxygen or sulphur atoms and optionally substituted by hydroxy, halogen, $C_1$-$C_4$-alkoxy, $C_1$-$C_4$-alkylthio, $C_3$-$C_6$-cycloalkyl, benzyl, furyl, tetrahydrofuryl, phenyl, halophenyl, $C_1$-$C_4$-alkylphenyl, $C_1$-$C_4$-alkoxyphenyl, nitrophenyl, cyano, carboxy, $C_1$-$C_4$-alkoxycarbonyl, $C_1$-$C_4$-alkylamino or di-$C_1$-$C_4$-alkylamino, a $C_3$-$C_8$-alkenyl or $C_3$-$C_8$-alkynyl group (each of which is optionally substituted by $C_3$-$C_8$-alkoxy, phenyl or halogen), $C_3$-$C_8$-cycloalkyl, optionally substituted by methyl, di-$C_1$-$C_4$-alkylmethylenimino or $C_3$-$C_6$-cycloalkylenimino;
$R^2$ and $R^3$, which may be the same or different, are $C_1$-$C_4$-alkyl, trifluoromethyl, $C_1$-$C_4$-alkoxy, $C_1$-$C_4$-alkoxy-$C_1$-$C_4$-alkyl, $C_1$-$C_4$-alkylthio, $C_1$-$C_4$-alkylamino, di-$C_1$-$C_4$-alkylamino or halogen;
$R^4$ is hydrogen, $C_1$-$C_{10}$-alkyl (optionally substituted by one or more of the same or different $C_1$-$C_4$-alkoxy, $C_1$-$C_4$-alkylthio, amino, $C_1$-$C_4$-alkylamino, di-$C_1$-$C_4$-alkylamino, nitro, halogen, phenyl or halophenyl), a $C_2$-$C_{10}$-alkenyl or $C_2$-$C_{10}$-alkynyl group (each of which is optionally substituted by one or more of the same or different $C_1$-$C_4$-alkoxy, $C_1$-$C_4$-alkylthio, amino, $C_1$-$C_4$-alkylamino, di-$C_1$-$C_4$-alkylamino, nitro, halogen or phenyl), or a $C_3$-$C_8$-cycloalkyl or $C_4$-$C_8$-cycloalkenyl group (each of which is optionally substituted by one or more of the same or different $C_1$-$C_4$-alkyl, $C_1$-$C_4$-alkoxy, $C_1$-$C_4$-alkylthio, amino, $C_1$-$C_4$-alkylamino, di-$C_1$-$C_4$-alkylamino, nitro, trifluoromethyl, halogen or phenyl);
$R^5$ has the same meaning as $R^4$ except hydrogen; or
$R^4$ and $R^5$ together with the carbon to which they are attached form a $C_3$-$C_8$-cycloalkyl group;
$R^6$ and $R^7$, which may be the same or different, are hydrogen or $C_1$-$C_4$-alkyl;
X is methine or nitrogen,
with the provisos,
a) A is not $-C\equiv N$, when $R^4$ and/or $R^5$ are methyl or benzyl,
b) $R^1$ is not ethyl, when $R^4$ is hydrogen and $R^5$ is benzyl, and
c) $R^5$ is not ethyl or allyl, when $R^1$ is hydrogen, $R^2$ and $R^3$ are each chlorine and X is nitrogen;
as well as their alkali metal, alkaline earth metal, ammonium and organic ammonium salts, and their optically active isomers, show interesting herbicidal, fungicidal and plant growth regulant activity.

The expression "halogen" means fluorine, chlorine, bromine and iodine. By the term alkali metal is meant lithium, sodium or potassium and by the term alkaline earth metal is meant calcium, strontium or barium.

The compounds of the invention of general formula I can be

A) by reacting a compound of general formula II

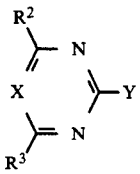

in which $R^2$, $R^3$ and X have the meanings given under general formula I, and Y is leaving group, such as halogen, alkylsulphonyl or phenylsulphonyl, with a compound of general formula III

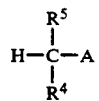

in which A, $R^4$ and $R^5$ have the meanings given under general formula I, in a suitable solvent in the presence of a suitable base, or B) by reacting a compound of general formula IV

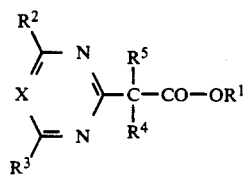

in which $R^1$, $R^2$, $R^3$, $R^4$, $R^5$ and X have the meanings given under general formula I, except for X being hydrogen, with an alkali metal base or alkaline earth metal base, in a suitable polar solvent, to give a compound of general formula V

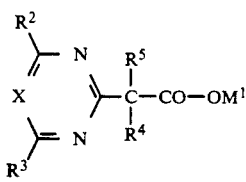

in which $R^2$, $R^3$, $R^4$, $R^5$ and X have the meanings given under general formula I and $M^1$ is an alkali metal atom or an equivalent of an alkaline earth metal atom, and optionally base, in a suitable polar in which A, $R^4$ and $R^5$ have the meanings given under general formula I, in a suitable solvent in the presence of a suitable base, or C) by reacting a compound of general formula V

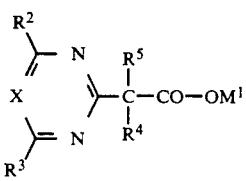

in which $R^2$, $R^3$, $R^4$, $R^5$, $M^1$ and X have the meanings in a suitable solvent, to give a compound of general formula VI

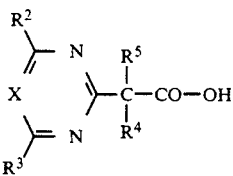

in which $R^2$, $R^3$, $R^4$, $R^5$ and X have the meanings given under general formula I, or D) by reacting a compound of general formula VI

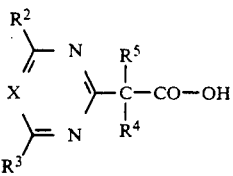

in which $R^2$, $R^3$, $R^4$, $R^5$ and X have the meanings given under general formula I, with a suitable base, in a formula VII

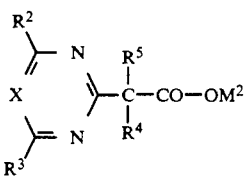

in which $R^2$, $R^3$, $R^4$, $R^5$ and X have the meanings given under general formula I and $M^2$ is an alkali metal atom or an equivalent of an alkaline earth metal atom, an ammonium ion or an organic ammonium group, or E) by reacting a compound of general formula VIII

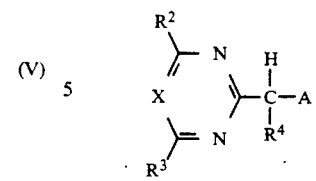

in which A, $R^2$, $R^3$, $R^4$ and X have the meanings given under general formula I, with a compound of general of formula IX

in which $R^5$ has the meaning given under general formula I, and Z is a leaving group, such as halogen, alkylsulphonyl, phenylsulphonyl or alkoxysulphonyloxy, in a suitable solvent, in the presence of a suitable base.

The individual process variants are preferably carried out in the presence of a diluent. For this, a solvent which is inert to the reactants is used.

Suitable solvents include water, aliphatic, alicyclic and aromatic hydrocarbons, that can be optionally chlorinated, such as for example hexane, cyclohexane, petroleum ether, ligroin, benzene, toluene, xylene, methylene chloride, chloroform, carbon tetrachloride, ethylene chloride and trichloroethane, ethers, such as for example diisopropyl ether, dibutyl ether, propylene oxide, dioxane and tetrahydrofuran; ketones, such as for example acetone, methyl ethyl ketone, methyl isopropyl ketone, nitriles, such as for example acetonitrile and propionitrile, alcohols, such as for example methanol, ethanol, isopropanol, butanol and ethylene glycol, esters, such as for example ethyl acetate and amyl acetate, amides, such as for example dimethylformamide and dimethylacetamide, sulphones and sulphoxides, such as for example dimethyl sulphoxide, and bases, such as for example pyridine.

The presence of a catalyst can be an advantage. Suitable catalysts include potassium iodide and onium compounds. such as quaternary ammonium, phosphonium and arsonium compounds as well as sulphonium compounds. Also suitable are polyglycol ethers, especially cyclic ethers, such as 18-crown-6, and tertiary amines, such as for example tributylamine. Preferred compounds are quaternary ammonium compounds, such as for example benzyltriethylammonium chloride and tetrabutylammonium bromide.

The reactions can be carried out under atmospheric pressure but if desired higher or lower pressures can be used.

The process variant A) is preferably carried out in an aprotic solvent such as benzene, toluene, xylene, tetrahydrofuran, diethyl ether, hexane, dimethylformamide or dimethyl sulphoxide.

Bases that can be used include sodium hydride, potassium tert-butylate or lithium diisopropylamide.

The reactions are suitably carried out between $-78°$ C. and the boiling point of the particular solvent or solvent mixture.

The reaction usually takes 5 minutes to 48 hours, preferably 0.5 to 24 hours.

Compounds of general formula II are described in the literature or can be prepared by methods analogous to those described in the literature.

For the processes variants B) and C), there is preferably used as a solvent an alcohol, such as ethanol, propanol or isopropanol, a ketone, such as acetone or methyl ethyl ketone, dimethylformamide or dimethyl sulphoxide, water or a polar solvent/water mixture.

Bases that can be used include for example, carbonates, such as sodium carbonate, potassium carbonate or calcium carbonate, or metal hydroxides, such as sodium hydroxide or potassium hydroxide.

The reaction temperature lies between room temperature and the boiling point of the particular solvent. The reaction time lies between 0.5 to 36 hours.

When $R^1$ in general formula IV is benzyl, a catalytic reduction (hydrogenation) of the compound of formula VI can also be used.

Suitable solvents for process variant D) include hydrocarbons, such as benzene, toluene or xylene, halogenated hydrocarbons, such as methylene chloride or chloroform, alcohols, such as methanol, ethanol or isopropanol, ethers, such as for example diethyl ether, diisopropyl ether, tetrahydrofuran or 1,4-dioxane, ketones, such as acetone or methyl ethyl ketone, esters, such as methyl acetate or ethyl acetate, or nitriles, such as acetonitrile.

Bases that can be used include an alkali metal, such as sodium or potassium, an alkali metal or alkaline earth metal hydride, such as sodium hydride, potassium hydride or calcium hydride, a carbonate, such as sodium carbonate, potassium carbonate or calcium carbonate, or a metal hydroxide, such as sodium hydroxide or potassium hydroxide. Organic ammonium bases that can be used include for example, ammonia an alkylamine (primary amine), a dialkylamine (secondary amine) or a trialkylamine (tertiary amine).

The temperature of the reaction falls within room temperature and the boiling point of the particular solvent or solvent mixture. The reaction time lies between 5 minutes and 10 hours.

The process variant E) is preferably carried out in an aprotic solvent, such as benzene, toluene, xylene, tetrahydrofuran, diethyl ether, hexane, dimethylformamide or dimethyl sulphoxide.

Bases that can be used include for example sodium hydride, potassium tert-butylate or lithium diisopropylamide.

The temperature of the reaction lies between $-78°$ C. and the boiling point of the particular solvent or solvent mixture.

The reaction time lies between 1 and 24 hours.

The compounds of the invention prepared by these processes can be isolated from the reaction mixtures in conventional manner, for example by distillation of the solvent at normal or reduced pressure, by precipitation with water or by extraction.

A higher level of purity can be achieved as a rule by column chromatography as well as by fractional distillation or crystallisation.

The compounds of the invention are, as a rule, colourless and odourless liquids or crystals that are soluble in water, slightly soluble in aliphatic hydrocarbons such as petroleum ether, hexane, pentane and cyclohexane and highly soluble in halogenated hydrocarbons, such as chloroform, methylene chloride and carbon tetrachloride, aromatic hydrocarbons, such as benzene, toluene and xylene, ethers, such as diethyl ether, tetrahydrofuran and dioxane, nitriles, such as acetonitrile, alcohols, such as methanol and ethanol, amides, such as dimethylformamide, and sulphoxides, such as dimethyl sulphoxide.

The compounds of the invention show a good herbicidal activity in broad leaved weeds and grasses. A selective use in various crops is possible, for example in such as rape, beets, soya beans, cotton, rice, barley, wheat and other cereals. Individual active substances are particularly suitable as selective herbicides in beet, cotton, soya and cereals. However the compounds can be used for control of weeds in permanent crops, such as for example forestry, ornamental trees, fruit, vine, citrus, nut, banana, coffee, tea, rubber, oil palm, cocoa, berry fruit and hop plantations and for the selective control of weeds in annual crops.

The compounds of the invention can used for example against the following plant species:

Dicotyledonous weeds of the species Sinapis, Lepidium, Galium, Stellaria, Matricaria, Anthemis, Galinsoga, Chenopodium, Brassica, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Lamium, Veronica, Abutilon, Datura, Viola, Galeopsis, Papaver, Centaurea and Chrysanthemum.

Monocotyledonous weeds of the species Avena, Alopecurus, Echinochloa, Setaria, Panicum, Digitaria, Poa, Eleusine, Brachiaria, Lolium, Bromus, Cyperus, Agropyron, Sagittaria, Monocharia, Fimbristylis, Eleocharis, Ischaemum and Apera.

The rates of use vary depending on the manner of pre- and postemergent use between 0.001 and 5 kg/ha.

The compounds of the invention can also be used as defoliants, desiccants and as total herbicides. They also influence plant growth and can thus be used to influence plant growth of crops. Some compounds also show fungicidal activity.

The compounds of the invention can be used either alone or in admixture with one another or with other active agents. Optionally, other plant-protective agents or pesticides can be added, depending on the purpose for the treatment. When it is desired to broaden the spectrum of activity, other herbicides can also be added. Herbicidally active mixing partners suitable in this connection include for example, the active agents listed in Weed Abstracts, vol. 38, No.3 (1989) under the heading "Lists of common names and abbreviations employed for currently used herbicides and plant growth regulators in Weed Abstracts".

An improvement in the intensity and speed of action can be obtained, for example, by addition of suitable adjuvants, such as organic solvents, wetting agents and oils. Such additives may allow a decrease in the dose.

The designated active ingredients or their mixtures can suitably be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example aliphatic and aromatic hydrocarbons, such as benzene, toluene, xylene, cyclohexanone, isophorone, dimethyl sulphoxide, dimethylformamide and other mineral-oil fractions and plant oils.

Suitable solid carriers include mineral earths, e.g. bentonite, silica gel, talc, kaolin, attapulgite, limestone, silicic acid and plant products, e.g. flours.

As surface-active agents there can be used for example calcium lignosulphonate, polyoxyethylenealkylphenyl ethers, naphthalenesulphonic acids and their salts, phenolsulphonic acids and their salts, formaldehyde condensates, fatty alcohol sulphates, as well as substituted benzenesulphonic acids and their salts.

The percentage of the active ingredient(s) in the various preparations can vary within wide limits. For example, the compositions can contain about 10 to 90 percent by weight active ingredients, and about 90 to 10 percent by weight liquid or solid carriers, as well as, optionally up to 20 percent by weight of surfactant.

The agents can be applied in customary fashion, for example with water as the carrier in spray mixture volumes of approximately 100 to 1,000 l/ha. The agents can be applied using low-volume or ultra-low-volume techniques or in the form of so-called microgranules.

The preparation of these formulations can be carried out in known manner, for example by milling or mixing processes. Optionally, individual components can be mixed just before use for example by the so-called commonly used tank-mixing method.

Formulations can be prepared, for example, from the following ingredients.

A) Wettable Powder
1) 25 percent by weight active ingredient
60 percent by weight kaolin
10 percent by weight silicic acid
5 percent by weight of a mixture of calcium lignosulphonate and the sodium salt of N-methyl-N-oleyltaurine
2) 40 percent by weight active ingredient
25 percent by weight bentonite
25 percent by weight colloidal silicic acid
10 percent by weight of a mixture of calcium lignosulphonate and alkylphenyl polyglycol ether B) Paste
45 percent by weight active ingredient
5 percent by weight sodium aluminium silicate
15 percent by weight cetyl polyglycol ether with 8 mol of ethylene oxide
2 percent by weight spindle oil
10 percent by weight polyethylene glycol
23 percent by weight water C) Emusifiable Concentrate
25 percent by weight active ingredient
15 percent by weight cyclohexanone
55 percent by weight xylene
5 percent by weight of a mixture of calcium dodecylbenzenesulphonate and nonylphenolpolyoxyethylene.

The following Examples illustrate the preparation of compounds of the invention.

EXAMPLE 1

Ethyl 2-(4,6-dimethoxypyrimidin-2-yl)pentanoate 4,2 g (30 mmol) Diisopropylamine in 100 ml tetrahydrofuran, under nitrogen at −78° C., was treated with 19 ml (30 mmol) 1.6M butyllithium in hexane. The mixture was stirred for 30 minutes and then at −60° C., a solution of 3.5 g (27 mmol) ethyl pentanoate, dissolved in 20 ml tetrahydrofuran, was added dropwise. The mixture was stirred for a further hour and 5.9 g (27 mmol) 4,6-dimethoxy-2-methylsulphonylpyrimidine was added, portionwise. The temperature of the mixture rose over 2 hours to +10° C. The reaction mixture was then washed with saturated aqueous ammonium chloride and sodium chloride. The aqueous phase was extracted with ethyl acetate. The organic phases were dried over magnesium sulphate and concentrated. The resulting yellow oil was finally purified on silica gel using a hexane/ethyl acetate mixture (0 to 20% ethyl acetate).

Yield: 3.2 g =42% of theory
$n^{20}_D$: 1.4824

EXAMPLE 2

2-(4,6-Dimethoxypyrimidin-2-yl)pentanoic acid

A mixture of 2.2 g (8 mmol) ethyl 2-(4,6-dimethoxypyrimidin-2-yl)pentanoate in 20 ml methanol and 3 ml 5N caustic soda was stirred overnight at room temperature. The mixture was concentrated and the residue dissolved in 10 ml water, extracted with 50 ml ethyl acetate and the aqueous phase acidified with 2N hydrochloric acid until it was pH 5. The aqueous phase was extracted three times with ether, the combined phases were dried over magnesium sulphate and concentrated.

Yield: 1.7 g=85% of theory
mp: 71°–73° C. (dec.)

EXAMPLE 3

Methyl 2,4-dimethyl-2-(4,6-dimethoxy-s-triazin-2-yl)pentanoate 0.5 g (17 mmol) Sodium hydride (80% in oil) was added at room temperature, under nitrogen, to a solution of 3.96 g (14 mmol) methyl 2-(4,6-dimethoxy-s-triazin-2-yl)pentanoate in 35 ml dimethylformamide. The mixture was stirred for one hour at room temperature and then 2.0 g (16 mmol) dimethyl sulphate was added dropwise. The mixture was left for 2.5 hours at room temperature, then added to 200 ml water and extracted twice with ethyl acetate. The combined organic phase was washed with saturated aqueous sodium chloride, dried over magnesium sulphate and concentrated. The crude product was purified by silica gel chromatography using a hexane/ethyl acetate mixture (0 to 20% ethyl acetate).

Yield: 2.3 g =62% of theory
$n^{20}_D$: 1.4775

In a similar manner the following compounds were prepared

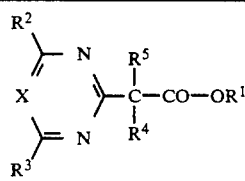

| Example No | $R^1$ | $R^2$ | $R^3$ | $R^4$ | $R^5$ | X | Physical constant |
|---|---|---|---|---|---|---|---|
| 4 | CH$_2$CH$_3$ | OCH$_3$ | OCH$_3$ | H | CH(CH$_3$)$_2$ | CH | $n_D^{20}$: 1.4794 |
| 5 | H | OCH$_3$ | OCH$_3$ | H | CH(CH$_3$)$_2$ | CH | mp: 109-110° C. (dec.) |
| 6 | CH$_3$ | OCH$_3$ | OCH$_3$ | H | Cyclohexyl | CH | $n_D^{20}$: 1.5028 |

-continued

| | | | | | | | | |
|---|---|---|---|---|---|---|---|---|
| 7 | CH$_2$CH$_3$ | OCH$_3$ | OCH$_3$ | H | Cyclohexyl | CH | $n_D^{20}$: 1.4982 |
| 8 | H | OCH$_3$ | OCH$_3$ | H | Cyclohexyl | CH | mp: 88–89° C. (dec.) |
| 9 | CH$_3$ | OCH$_3$ | OCH$_3$ | H | C(CH$_3$)$_3$ | CH | $n_D^{20}$: 1.4868 |
| 10 | CH$_2$CH$_3$ | OCH$_3$ | OCH$_3$ | H | (CH$_2$)$_4$CH$_3$ | CH | $n_D^{20}$: 1.4755 |
| 11 | H | OCH$_3$ | OCH$_3$ | H | (CH$_2$)$_4$CH$_3$ | CH | $n_D^{20}$: 1.4920 |
| 12 | CH$_3$ | OCH$_3$ | OCH$_3$ | H | (CH$_2$)$_2$SCH$_3$ | CH | $n_D^{20}$: 1.5175 |
| 13 | CH$_2$CH$_3$ | OCH$_3$ | OCH$_3$ | H | CH$_2$CH(CH$_3$)$_2$ | CH | $n_D^{20}$: 1.4773 |
| 14 | CH$_2$CH$_3$ | Cl | OCH$_3$ | H | CH(CH$_3$)$_2$ | CH | $n_D^{20}$: 1.4926 |
| 15 | CH$_2$CH$_3$ | OCH$_3$ | OCH$_3$ | H | CH(CH$_3$)$_2$ | N | $n_D^{20}$: 1.4796 |
| 16 | CH$_2$CH$_3$ | CH$_3$ | CH$_3$ | H | CH(CH$_3$)$_2$ | CH | $n_D^{20}$: 1.4803 |
| 17 | CH$_2$CH$_3$ | CH$_3$ | CF$_3$ | H | CH(CH$_3$)$_2$ | CH | $n_D^{20}$: 1.4406 |
| 18 | CH$_2$CH$_3$ | CH$_3$ | OCH$_3$ | H | CH(CH$_3$)$_2$ | CH | $n_D^{20}$: 1.4794 |
| 19 | CH$_3$ | OCH$_3$ | OCH$_3$ | CH$_3$ | (CH$_2$)$_2$CH$_3$ | CH | $n_D^{20}$: 1.4829 |
| 20 | CH$_2$CH$_3$ | OCH$_3$ | OCH$_3$ | H | CH$_2$CH(CH$_3$)$_2$ | N | $n_D^{20}$: 1.4740 |
| 21 | CH$_2$CH$_3$ | OCH$_3$ | OCH$_3$ | H | CH$_3$ | CH | $n_D^{20}$: 1.4808 |
| 22 | CH$_3$ | OCH$_3$ | OCH$_3$ | H | (CH$_2$)CH$_3$ | CH | $n_D^{20}$: 1.4834 |
| 23 | CH$_3$ | OCH$_3$ | OCH$_3$ | H | CH(CH$_3$)$_2$ | N | $n_D^{20}$: 1.4834 |
| 24 | H | OCH$_3$ | OCH$_3$ | H | C(CH$_3$)$_3$ | N | mp: 82–83° C. (dec.) |
| 25 | CH$_3$ | OCH$_3$ | OCH$_3$ | H | CH$_2$CH=CH$_2$ | N | $n_D^{20}$: 1.4966 |
| 26 | CH$_2$CH$_3$ | OCH$_3$ | OCH$_3$ | H | CH$_2$CH=CH$_2$ | N | $n_D^{20}$: 1.4882 |
| 27 | H | OCH$_3$ | OCH$_3$ | H | CH$_2$CH=CH$_2$ | N | mp: 71–73° C. |
| 28 | H | OCH$_3$ | OCH$_3$ | H | CH$_2$CH(CH$_3$)$_2$ | N | mp: 86–88° C. |
| 29 | CH$_2$CH$_3$ | OCH$_3$ | OCH$_3$ | H | (CH$_2$)$_2$C≡CH | N | $n_D^{20}$: 1.4903 |
| 30 | H | OCH$_3$ | OCH$_3$ | H | (CH$_2$)$_2$C≡CH | N | mp: 73–75° C. (dec.) |
| 31 | CH$_3$ | OCH$_3$ | OCH$_3$ | H | CH(CH$_3$)$_2$ | N | $n_D^{20}$: 1.4815 |
| 32 | CH$_2$(CH$_3$)$_2$ | OCH$_3$ | OCH$_3$ | H | CH(CH$_3$)$_2$ | N | $n_D^{20}$: 1.4744 |
| 33 | Tetrahydrofurfuryl | OCH$_3$ | OCH$_3$ | H | CH(CH$_3$)$_2$ | N | $n_D^{20}$: 1.4946 |
| 34 | CH$_2$C≡CH | OCH$_3$ | OCH$_3$ | H | CH(CH$_3$)$_2$ | N | $n_D^{20}$: 1.4922 |
| 35 | CH$_2$CH=C—(CH$_3$)C≡CH | OCH$_3$ | OCH$_3$ | H | CH(CH$_3$)$_2$ | N | $n_D^{20}$: 1.5021 |
| 36 | H$_3$NCH(CH$_3$)$_2$ | OCH$_3$ | OCH$_3$ | H | CH(CH$_3$)$_2$ | N | mp: 127° C. (dec.) |
| 37 | N=C(CH$_3$)$_2$ | OCH$_3$ | OCH$_3$ | H | CH(CH$_3$)$_2$ | N | $n_D^{20}$: 1.4895 |
| 38 | CH$_2$OCH$_3$ | OCH$_3$ | OCH$_3$ | H | CH(CH$_3$)$_2$ | N | $n_D^{20}$: 1.4782 |
| 39 | CH$_2$C≡CH | OCH$_3$ | OCH$_3$ | H | C(CH$_3$)$_3$ | N | mp: 72–74° C. (dec.) |
| 40 | CH$_2$CH=C—(CH$_3$)C≡CH | OCH$_3$ | —OCH$_3$ | H | C(CH$_3$)$_3$ | N | $n_D^{20}$: 1.5049 |
| 41 | CH$_3$ | OCH$_3$ | N(CH$_3$)$_2$ | H | CH(CH$_3$)$_2$ | N | mp: 46° C. |
| 42 | CH$_3$ | CH$_2$OCH$_3$ | OCH$_3$ | H | CH(CH$_3$)$_2$ | CH | $n_D^{20}$: 1.4805 |
| 43 | CH$_3$ | OCH$_3$ | OCH$_3$ | | —(CH$_2$)$_5$— | CH | $n_D^{20}$: 1.5056 |
| 44 | H | OCH$_3$ | OCH$_3$ | | —(CH$_2$)$_5$— | CH | mp: 88–90° C. |
| 45 | CH$_2$CH$_3$ | OCH$_3$ | OCH$_3$ | | —(CH$_2$)$_5$— | CH | $n_D^{20}$: 1.4928 |
| 46 | H | OCH$_3$ | OCH$_3$ | | —(CH$_2$)$_3$— | CH | mp: 120–121° C. (dec.) |
| 47 | CH$_2$CH$_3$ | OCH$_3$ | OCH$_3$ | CH$_2$—CH=CH$_2$ | CH$_2$CH(CH$_3$)$_2$ | N | $n_D^{20}$: 1.4856 |
| 48 | CH$_3$ | OCH$_3$ | OCH$_3$ | H | (CH$_2$)$_3$CH$_3$ | N | $n_D^{20}$: 1.4716 |
| 49 | CH$_3$ | OCH$_3$ | OCH$_3$ | H | CH$_2$CH(CH$_3$)$_2$ | N | $n_D^{20}$: 1.4794 |
| 50 | H | OCH$_3$ | OCH$_3$ | CH$_3$ | (CH$_2$)$_2$CH$_3$ | CH | mp: 68–70° C. |
| 51 | CH$_2$CH$_3$ | OCH$_3$ | OCH$_3$ | CH$_3$ | CH(CH$_3$)$_2$ | CH | $n_D^{20}$: 1.4813 |
| 52 | CH$_2$CH$_3$ | OCH$_3$ | OCH$_3$ | CH$_3$ | CH$_2$CH=CH$_2$ | CH | $n_D^{20}$: 1.4884 |
| 53 | CH$_3$ | OCH$_3$ | OCH$_3$ | H | (CH$_2$)$_3$CH$_3$ | CH | $n_D^{20}$: 1.3769 |
| 54 | CH$_2$CH$_3$ | OCH$_3$ | OCH$_3$ | H | (CH$_2$)$_3$CH$_3$ | CH | $n_D^{20}$: 1.4781 |
| 55 | H | OCH$_3$ | OCH$_3$ | H | (CH$_2$)$_3$CH$_3$ | CH | mp: 71–72° C. |
| 56 | N=C(CH$_3$)$_2$ | OCH$_3$ | OCH$_3$ | H | (CH$_2$)$_3$CH$_3$ | CH | $n_D^{20}$: 1.4972 |
| 57 | CH$_3$ | OCH$_3$ | OCH$_3$ | CH$_2$—C≡CH | CH$_2$C≡CH | CH | mp: 70–73° C. |
| 58 | CH$_3$ | OCH$_3$ | OCH$_3$ | H | (CH$_2$)$_2$CH$_3$ | N | $n_D^{20}$: 1.4844 |
| 59 | CH$_3$ | OCH$_3$ | OCH$_3$ | H | Cyclopropylmethyl | CH | $n_D^{20}$: 1.4973 |
| 60 | CH$_3$ | OCH$_3$ | OCH$_3$ | H | CH(CH$_3$)—CH$_2$CH$_3$ | CH | $n_D^{20}$: 1.4846 |
| 61 | CH$_2$CH$_3$ | OCH$_3$ | OCH$_3$ | H | CH(CH$_3$)—CH$_2$CH$_3$ | CH | $n_D^{20}$: 1.4796 |
| 62 | CH$_3$ | OCH$_3$ | OCH$_3$ | H | CH(CH$_3$)—CH$_2$CH$_3$ | N | $n_D^{20}$: 1.4864 |
| 63 | CH$_2$CH$_3$ | OCH$_3$ | OCH$_3$ | H | CH(CH$_3$)—CH$_2$CH$_3$ | N | $n_D^{20}$: 1.4777 |
| 64 | Tetrahydrofurfuryl | OCH$_3$ | OCH$_3$ | H | CH(CH$_3$)$_2$ | N | $n_D^{20}$: 1.4903 |
| 65 | H | OCH$_3$ | OCH$_3$ | H | CH$_3$ | CH | mp: 79°C. (dec.) |
| 66 | CH$_2$CH$_3$ | OCH$_3$ | OCH$_3$ | H | CH$_2$CH$_3$ | CH | $n_D^{20}$: 1.4816 |
| 67 | CH$_2$CH$_3$ | OCH$_3$ | OCH$_3$ | H | CH$_2$CH$_3$ | CH | $n_D^{20}$: 1.4807 |
| 68 | H | OCH$_3$ | OCH$_3$ | H | CH(CH$_3$)—CH$_2$CH$_3$ | CH | mp: 82° C. (dec.) |
| 69 | H | OCH$_3$ | OCH$_3$ | H | CH$_2$CH$_3$ | CH | mp: 97° C. (dec.) |
| 70 | N=C(CH$_3$)$_2$ | OCH$_3$ | OCH$_3$ | H | CH(CH$_3$)—CH$_2$CH$_3$ | CH | mp: 124° C. (dec.) |
| 71 | N=C(CH$_3$)$_2$ | OCH$_3$ | OCH$_3$ | H | (CH$_2$)$_2$CH$_3$ | CH | $n_D^{20}$: 1.4974 |
| 72 | N=C(CH$_3$)—CH$_2$CH$_3$ | OCH$_3$ | OCH$_3$ | H | CH(CH$_3$)$_2$ | CH | $n_D^{20}$: 1.4946 |
| 73 | Benzyl | OCH$_3$ | OCH$_3$ | H | CH(CH$_3$)$_2$ | N | $n_D^{20}$: 1.5226 |
| 74 | Benzyl | OCH$_3$ | Cl | H | CH(CH$_3$)$_2$ | N | $n_D^{20}$: 1.5351 |
| 75 | (CH$_2$)$_2$O—N=C(CH$_3$)$_2$ | OCH$_3$ | OCH$_3$ | H | CH(CH$_3$)$_2$ | CH | $n_D^{20}$: 1.4852 |
| 76 | CH$_2$CH$_3$ | OCH$_2$CH$_3$ | OCH$_2$CH$_3$ | H | CH(CH$_3$)$_2$ | CH | $n_D^{20}$: 1.4758 |
| 77 | CH$_2$CH$_3$ | OCH$_3$ | Cl | H | CH(CH$_3$)$_2$ | N | $n_D^{20}$: 1.4891 |

-continued

| | | | | | | | |
|---|---|---|---|---|---|---|---|
| 78 | CH$_2$CH$_3$ | OCH$_3$ | (CH$_2$)$_3$CH$_3$ | H | CH(CH$_3$)$_2$ | N | n$_D^{20}$: 1.4685 |
| 79 | (CH$_2$)$_2$—N(CH$_3$)$_2$ | OCH$_3$ | OCH$_3$ | H | CH(CH$_3$)$_2$ | N | n$_D^{20}$: 1.4850 |
| 80 | (CH$_2$)$_2$—N(CH$_2$)$_5$ | OCH$_3$ | OCH$_3$ | H | CH(CH$_3$)$_2$ | N | n$_D^{20}$: 1.4967 |
| 81 | (CH$_2$)$_3$CH$_3$ | OCH$_3$ | OCH$_3$ | H | CH(CH$_3$)$_2$ | N | n$_D^{20}$: 1.4763 |
| 82 | (CH$_2$)$_2$O—CH$_2$CH$_3$ | OCH$_3$ | OCH$_3$ | H | CH(CH$_3$)$_2$ | N | n$_D^{20}$: 1.4755 |
| 83 | (CH$_2$)$_2$O—(CH$_2$)$_2$O—CH$_2$CH$_3$ | OCH$_3$ | OCH$_3$ | H | CH(CH$_3$)$_2$ | N | n$_D^{20}$: 1.4759 |
| 84 | (CH$_2$)$_2$O-benzyl | OCH$_3$ | OCH$_3$ | H | CH(CH$_3$)$_2$ | N | n$_D^{20}$: 1.5166 |
| 85 | (CH$_2$)$_2$OH | OCH$_3$ | OCH$_3$ | H | CH(CH$_3$)$_2$ | N | n$_D^{20}$: 1.4972 |
| 86 | CH$_2$CO$_2$H | OCH$_3$ | OCH$_3$ | H | CH(CH$_3$)$_2$ | N | |
| 87 | CH$_2$CO$_2$CH$_3$ | OCH$_3$ | OCH$_3$ | H | CH(CH$_3$)$_2$ | N | |
| 88 | H | OCH$_3$ | OCH$_3$ | H | 1-Methylbenzyl | CH | mp: 141° C. (dec.) |
| 89 | CH$_3$ | OCH$_3$ | OCH$_3$ | H | 1-Methylbenzyl | CH | mp: 81° C. |
| 90 | CH$_2$CH$_3$ | OCH$_2$CH$_3$ | OCH$_3$ | H | CH(CH$_3$)$_2$ | N | n$_D^{20}$: 1.4732 |
| 91 | CH$_2$CO$_2$CH$_3$ | OCH$_3$ | OCH$_3$ | H | CH(CH$_3$)$_2$ | CH | n$_D^{20}$: 1.4859 |
| 92 | CH(CH$_3$)—CO$_2$CH$_3$ | OCH$_3$ | OCH$_3$ | H | CH(CH$_3$)$_2$ | CH | n$_D^{20}$: 1.4809 |
| 93 | (CH$_2$)$_2$—N(CH$_3$)$_3$J | OCH$_3$ | OCH$_3$ | H | CH(CH$_3$)$_2$ | N | mp: 74–76° C. |
| 94 | CH$_2$CH$_3$ | OCH$_3$ | OCH$_2$CH$_3$ | H | CH(CH$_3$)$_2$ | N | n$_D^{20}$: 1.4746 |
| 95 | CH$_2$CH$_3$ | CH$_3$ | OCH$_3$ | H | CH(CH$_3$)$_2$ | N | n$_D^{20}$: 1.4773 |
| 96 | CH$_2$CH$_3$ | OCH$_3$ | OCH(CH$_3$)$_2$ | H | CH(CH$_3$)$_2$ | N | n$_D^{20}$: 1.4724 |
| 97 | CH$_2$CH$_3$ | OCH(CH$_3$)$_2$ | OCH(CH$_3$)$_2$ | H | CH(CH$_3$)$_2$ | N | n$_D^{20}$: 1.4688 |
| 98 | CH$_3$ | OCH$_3$ | OCH$_3$ | H | Benzyl | CH | n$_D^{24}$: 1.5350 |
| 99 | CH$_3$ | OCH$_3$ | OCH$_3$ | Benzyl | Benzyl | CH | mp: 107–109° C. |
| 100 | H | OCH$_3$ | OCH$_3$ | H | Benzyl | CH | mp: 100–104° C. |
| 101 | CH$_3$ | OCH$_3$ | OCH$_3$ | 3-Chlorobenzyl | 3-Chlorobenzyl | CH | n$_D^{20}$: 1.5660 |
| 102 | CH$_3$ | OCH$_3$ | OCH$_3$ | H | 3-Chlorobenzyl | CH | n$_D^{24}$: 1.5410 |
| 103 | CH$_3$ | OCH$_3$ | OCH$_3$ | 4-Chlorobenzyl | 4-Chlorobenzyl | CH | mp: 122–125° C. |
| 104 | H | OCH$_3$ | OCH$_3$ | H | 3-Chlorobenzyl | CH | mp: 117–118° C. |
| 105 | CH$_3$ | OCH$_3$ | OCH$_3$ | H | 4-Chlorobenzyl | CH | mp: 66–68° C. |
| 106 | H | OCH$_3$ | OCH$_3$ | H | 4-Chlorobenzyl | CH | mp: 103–104° C. |
| 107 | CH$_3$ | OCH$_3$ | OCH$_3$ | (CH$_2$)$_3$CH$_3$ | (CH$_2$)$_3$CH$_3$ | CH | n$_D^{24}$: 1.4780 |
| 108 | CH$_3$ | OCH$_3$ | OCH$_3$ | H | CH$_2$C≡CH | CH | n$_D^{24}$: 1.5020 |
| 109 | (CH$_2$)$_3$—CO$_2$CH$_2$CH$_3$ | OCH$_3$ | OCH$_3$ | H | CH(CH$_3$)$_2$ | CH* | n$_D^{20}$: 1.4768 |

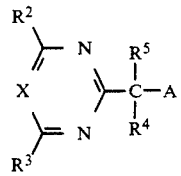

| Example No | A | R$^2$ | R$^3$ | R$^4$ | R$^5$ | X | constant |
|---|---|---|---|---|---|---|---|
| 110 | CN | OCH$_3$ | OCH$_3$ | H | CH(CH$_3$)$_2$ | CH | n$_D^{20}$: 1.4930 |
| 111 | CONH$_2$ | OCH$_3$ | OCH$_3$ | H | (CH$_2$)$_3$CH$_3$ | CH | mp: 75–76° C. |
| 112 | CONH$_2$ | OCH$_3$ | OCH$_3$ | H | CH(CH$_3$)$_2$ | CH | mp: 103–105° C. |
| 113 | CON(CH$_3$)$_2$ | OCH$_3$ | OCH$_3$ | H | CH(CH$_3$)$_2$ | CH | n$_D^{20}$: 1.5030 |
| 114 | CON(C$_2$H$_5$)$_2$ | OCH$_3$ | OCH$_3$ | H | CH(CH$_3$)$_2$ | CH | n$_D^{20}$: 1.4960 |

The following examples illustrate the possibilities for use of the compounds of the invention.

EXAMPLE A

In a greenhouse, the noted plant species were treated pre-emergently with the noted compounds of the invention, at a rate of 0.3 kg active ingredient/ha. The compounds of the invention were sprayed evenly over the soil as emulsions or suspensions in 500 liters water/ha. Three weeks after the treatment, the compounds of the invention showed excellent activity against the weeds. The comparison material did not show similar high efficacy.

In the following table:

```
           0 = no damage
           1 = 1–24% damage
           2 = 25–74% damage
           3 = 75–89% damage
           4 = 90–100% damage
   AGRRE = Elymus repens
   BROTE = Bromus tectorum
   SORHA = Sorghum halepense
   ABUTH = Abutilon theophrasti
   IPOSS = Ipomoea purpurea
   SEBEX = Sesbania exaltata
```

| Compound of the invention | AGRRE | BROTE | SORHA | ABUTH | IPOSS | SEBEX |
|---|---|---|---|---|---|---|
| Example 5 | 3 | 4 | 3 | 3 | 3 | 3 |
| Example 15 | 3 | 4 | 3 | 3 | 3 | 3 |
| Example 23 | 3 | 4 | 3 | — | 3 | 3 |
| Example 33 | 3 | 3 | 3 | 2 | 2 | 2 |
| Example 36 | 3 | 4 | 4 | 3 | 2 | 3 |
| Example 62 | 3 | 4 | 3 | — | — | 2 |
| Example 63 | 3 | 3 | 3 | 3 | — | 3 |
| Example 64 | 3 | 3 | 3 | 3 | 2 | 3 |
| Example 70 | 3 | 4 | 3 | 4 | 3 | 3 |
| Example 72 | 3 | 4 | 3 | 3 | 2 | 3 |
| Example 73 | 3 | 4 | 3 | 4 | 2 | 3 |
| Untreated Comparison | 0 | 0 | 0 | 0 | 0 | 0 |
| Imazamethabenz | 1 | 2 | 2 | 2 | 2 | 1 |

EXAMPLE B

In a greenhouse, the noted plant species were treated post-emergently with the noted compounds of the invention, at a rate of 0.1 kg active ingredient/ha. The compounds of the invention were sprayed evenly over the plants as emulsions or suspensions in 500 liters water/ha. Two weeks after the treatment, the compounds of the invention showed a high crop selectivity in wheat and maize with excellent activity against the weeds. The comparison material did not show similar high efficacy.

In the following table:

```
0 = no damage
1 = 1-24% damage
2 = 25-74% damage
3 = 75-89% damage
4 = 90-100% damage
GLMXA = Glycine maxima
GOSHI = Gossypium hirsutum
HELAN = Helianthus annuus
TRZAX = Triticum aestivum
BROTE = Bromus tectorum
GALAP = Galium aparine
VERPE = Veronica persica
VIOSS = Viola sp
```

| Compound of the invention | GLMXA | GOSHI | HELAN | TRZAX | BROTE | GALAP | VERPE | VIOSS |
|---|---|---|---|---|---|---|---|---|
| Example 5 | 0 | 0 | 0 | 1 | 3 | 3 | 3 | 3 |
| Untreated Comparison | 0 | 0 | 0 | 0 | 0 | 0 | 0 | 0 |
| Imazamethabenz | 0 | 1 | 1 | 0 | 0 | 1 | 2 | 1 |

EXAMPLE C

In a greenhouse, the noted plant species were treated pre-emergently with the noted compounds of the invention, at a rate of 0.3 kg active ingredient/ha. The compounds of the invention were sprayed evenly over the soil as emulsions or suspensions in 500 liters water/ha. Three weeks after the treatment, the compounds of the invention showed excellent activity against the weeds. The comparison material did not show similar high efficacy.

In the following table:

```
0 = no damage
1 = 1-24% damage
2 = 25-74% damage
3 = 75-89% damage
4 = 90-100% damage
GLMXA = Glycine maxima
GOSHI = Gossypium hirsutum
HELAN = Helianthus annuus
BROTE = Bromus tectorum
PANSS = Panicum maximum
```

| Compound of the invention | GLMXA | GOSHI | HELAN | BROTE | PANSS |
|---|---|---|---|---|---|
| Example 4 | 0 | 0 | 0 | 3 | 3 |
| Example 8 | 1 | 1 | 1 | 3 | 3 |
| Example 20 | 1 | — | 0 | 3 | 3 |
| Example 31 | 0 | 0 | 1 | 3 | 3 |
| Example 32 | 0 | 1 | 1 | — | 3 |
| Example 34 | 0 | — | 1 | 3 | 3 |
| Example 35 | 0 | — | 0 | 3 | 3 |
| Example 37 | 0 | 0 | 0 | 3 | 3 |
| Example 38 | — | — | 1 | 3 | 3 |
| Example 60 | 1 | 0 | 0 | 3 | 3 |
| Example 61 | 0 | 0 | 0 | 3 | 3 |
| Example 68 | 1 | 1 | 1 | — | 3 |
| Example 71 | — | 1 | 1 | 3 | 3 |
| Example 75 | 0 | — | 1 | 3 | 3 |
| Untreated Comparison | 0 | 0 | 0 | 0 | 0 |
| Imazamethabenz | 1 | 0 | 0 | 0 | 1 |

EXAMPLE D

In a greenhouse, the noted plant species were treated pre-emergently with the noted compounds of the invention, at a rate of 0.1 kg active ingredient/ha. The compounds of the invention were sprayed evenly over the soil as emulsions or suspensions in 500 liters water/ha. Three weeks after the treatment, the compounds of the invention showed excellent activity against the weeds. The comparison material did not show similar high efficacy.

In the following table:

```
0 = no damage
1 = 1-24% damage
2 = 25-74% damage
3 = 75-89% damage
4 = 90-100% damage
TRZAX = Triticum aestivum
VERPE = Veronica persica
VIOSS = Viola sp
```

| Compound of the invention | TRZAX | VERPE | VIOSS |
|---|---|---|---|
| Example 22 | 0 | 3 | 3 |
| Untreated Comparison | 0 | 0 | 0 |
| Imazamethabenz | 0 | 1 | 2 |

EXAMPLE E

In a greenhouse, the noted plant species were treated pre-emergently with the noted compounds of the invention, at a rate of 1.0 kg active ingredient/ha. The compounds of the invention were sprayed evenly over the soil as emulsions or suspensions in 500 liters water/ha. Three weeks after the treatment, the compounds of the invention showed excellent activity against the weeds. The comparison material did not show similar high efficacy.

In the following table:

```
0 = no damage
```

-continued

```
1 = 1-24% damage
2 = 25-74% damage
3 = 75-89% damage
4 = 90-100% damage
GLMXA = Glycine maxima
GOSHI = Gossypium hirsutum
ZEAMX = Zea mays
BROTE = Bromus tectorum
SETVI = Setaria viridis
GALAP = Galium aparine
MATCH = Matricaria chamomilla
VERPE = Veronica persica
VIOSS = Viola sp
```

| Compound of the invention | GLXMA | GOSHI | ZEAMX | BROTE | SETVI | GALAP | MATCH | VERPE | VIOSS |
|---|---|---|---|---|---|---|---|---|---|
| Example 24 | 0 | 0 | 0 | 3 | 3 | 3 | 3 | 3 | 3 |
| Example 59 | 0 | 1 | — | — | 3 | 3 | — | 3 | 3 |
| Example 67 | 1 | 0 | 1 | 3 | — | 3 | — | 3 | 3 |
| Untreated | 0 | 0 | 0 | 0 | 0 | 0 | 0 | 0 | 0 |
| Comparison Imazamethabenz | 3 | 2 | 2 | 2 | 3 | 3 | 3 | 3 | 3 |

We claim:

1. A herbicidal composition which comprises a compound of formula I

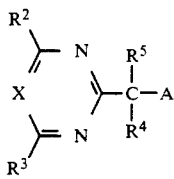

in which

A is one of the groups $-CO-OR^1$, $-CO-NR^6R^7$ or $-C\equiv N$, $R^1$ is hydrogen, $C_1-C_{12}$-alkyl (optionally substituted by hydroxy, halogen, $C_1-C_4$-alkoxy, $C_1-C_4$-alkylthio, $C_3-C_6$-cycloalkyl, benzyl, furyl, tetrahydrofuryl, phenyl, halophenyl, $C_1-C_4$-alkylphenyl, $C_1-C_4$-alkoxyphenyl, nitrophenyl, cyano, carboxy, $C_1-C_4$-alkoxycarbonyl, $C_1-C_4$-alkylamino, di-$C_1-C_4$-alkylamino, tri-$C_1-C_4$-alkylammoniumhalide, $C_2-C_5$-alkylenimino or di-$C_1-C_4$-alkylmethyleniminooxy), $C_2-C_{12}$-alkyl, interrupted by one or more oxygen or sulphur atoms and optionally substituted by hydroxy, halogen, $C_1-C_4$-alkoxy, $C_1-C_4$-alkylthio, $C_3-C_6$-cycloalkyl, benzyl, furyl, tetrahydrofuryl, phenyl, halophenyl, $C_1-C_4$-alkylphenyl, $C_1-C_4$-alkoxyphenyl, nitrophenyl, cyano, carboxy, $C_1-C_4$-alkoxycarbonyl, $C_1-C_4$-alkylamino or di-$C_1-C_4$-alkylamino, a $C_3-C_8$-alkenyl or $C_3-C_8$-alkynyl group (each of which is optionally substituted by $C_3-C_8$-alkoxy, phenyl or halogen), $C_3-C_8$-cycloalkyl, optionally substituted by methyl, di-$C_1-C_4$-alkylmethylenimino or $C_3-C_6$-cycloalkylenimino;

$R^2$ and $R^3$, which may be the same or different, are $C_1-C_4$-alkyl, trifluoromethyl, $C_1-C_4$-alkoxy, $C_1-C_4$-alkoxy-$C_1-C_4$-alkyl, $C_1-C_4$-alkylthio, $C_1-C_4$-alkylamino, di-$C_1-C_4$-alkylamino or halogen;

$R^4$ is hydrogen, $C_1-C_{10}$-alkyl (optionally substituted by one or more of the same or different $C_1-C_4$-alkoxy, $C_1-C_4$-alkylthio, amino, $C_1-C_4$-alkylamino, di-$C_1-C_4$-alkylamino, nitro, halogen, phenyl or halophenyl), a $C_2-C_{10}$-alkenyl or $C_2-C_{10}$-alkynyl group (each of which is optionally substituted by one or more of the same or different $C_1-C_4$-alkoxy, $C_1-C_4$-alkylthio, amino, $C_1-C_4$-alkylamino, di-$C_1-C_4$-alkylamino, nitro, halogen or phenyl), or a $C_3-C_8$-cycloalkyl or $C_4-C_8$-cycloalkenyl group (each of which is optionally substituted by one or more of the same or different $C_1-C_4$-alkyl, $C_1-C_4$-alkoxy, $C_1-C_4$-alkylthio, amino, $C_1-C_4$-alkylamino, di-$C_1-C_4$-alkylamino, nitro, trifluoromethyl, halogen or phenyl);

$R^5$ has the same meaning as $R^4$ except hydrogen; or $R^4$ and $R^5$ together with the carbon to which they are attached form a $C_3-C_8$-cycloalkyl group;

$R^6$ and $R^7$, which may be the same or different, are hydrogen or $C_1-C_4$-alkyl;

X is methine, with the provisos, a) A is not $-C\equiv N$, when $R^4$ and/or $R^5$ are methyl or benzyl, and b) $R^1$ is not ethyl, when $R^4$ is hydrogen and $R^5$ is benzyl, as well as its alkali metal, alkaline earth metal, ammonium and organic ammonium salts, and their optically active isomers, in admixture with agricultural acceptable carriers or diluents.

2. A method of combating weeds which comprises applying to the weeds r their locus a compound of formula I

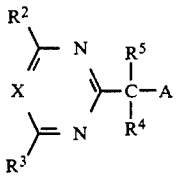

in which

A is one of the groups $-CO-OR^1$, $-CO-NR^6R^7$ or $-C\equiv N$, $R^1$ is hydrogen, $C_1-C_{12}$-alkyl (optionally substituted by hydroxy, halogen, $C_1-C_4$-alkoxy, $C_1-C_4$-alkylthio, $C_3-C_6$-cycloalkyl, benzyl, furyl, tetrahydrofuryl, phenyl, halophenyl, $C_1-C_4$-alkylphenyl, $C_1-C_4$-alkoxyphenyl, nitrophenyl, cyano, carboxy, $C_1-C_4$-alkoxycarbonyl, $C_1-C_4$-alkylamino, di-$C_1-C_4$-alkylamino, tri-$C_1-C_4$-alkylammoniumhalide, $C_2-C_5$-alkylenimino or di-$C_1-C_4$-alkylmethyleniminooxy), $C_2-C_{12}$-alkyl, interrupted by one or more oxygen or sulphur atoms and optionally substituted by hydroxy, halogen, $C_1-C_4$-alkoxy, $C_1-C_4$-alkylthio, $C_3-C_6$-cycloalkyl, benzyl, furyl, tetrahydrofuryl, phenyl, halophenyl, $C_1-C_4$-alkylphenyl, $C_1-C_4$-alkoxyphenyl, nitrophenyl, cyano, carboxy, $C_1-C_4$-alkoxycarbonyl, $C_1-C_4$-alkylamino or di-$C_1-C_4$-alkylamino, a $C_3-C_8$-alkenyl or $C_3-C_8$-alkynyl group (each of which is optionally substituted by $C_3-C_8$-alkoxy, phenyl or halogen), $C_3-C_8$-cycloalkyl, optionally substituted by methyl, di-$C_1-C_4$-alkylmethylenimino or $C_3-C_6$-cycloalkylenimino;

$R^2$ and $R^3$, which may be the same or different, are $C_1-C_4$-alkyl, trifluoromethyl, $C_1-C_4$-alkoxy, $C_1-C_4$-alkoxy-$C_1-C_4$-alkyl, $C_1-C_4$-alkylthio, $C_1-C_4$-alkylamino, di-$C_1-C_4$-alkylamino or halogen;

$R^4$ is hydrogen, $C_1-C_{10}$-alkyl (optionally substituted by one or more of the same or different $C_1-C_4$-alkoxy, $C_1$-$C_4$-alkylthio, amino, $C_1$-$C_4$-alkylamino, di-$C_1$-$C_4$-alkylamino, nitro, halogen, phenyl or halophenyl), a $C_2$-$C_{10}$-alkenyl or $C_2$-$C_{10}$-alkynyl group (each of which is optionally substituted by one or more of the same or different $C_1$-$C_4$-alkoxy, $C_1$-$C_4$-alkylthio, amino, $C_1$-$C_4$-alkylamino, di-$C_1$-$C_4$-alkylamino, nitro, halogen or phenyl), or a $C_3$-$C_8$-cycloalkyl or $C_4$-$C_8$-cycloalkenyl group (each of which is optionally substituted by one or more of the same or different $C_1$-$C_4$-alkyl, $C_1$-$C_4$-alkoxy, $C_1$-$C_4$-alkylthio, amino, $C_1$-$C_4$-alkylamino, di-$C_1$-$C_4$-alkylamino, nitro, trifluoromethyl, halogen or phenyl);

$R^5$ has the same meaning as $R^4$ except hydrogen; or $R^4$ and $R^5$ together with the carbon to which they are attached form a $C_3$-$C_8$-cycloalkyl group;

$R^6$ and $R^7$, which may be the same or different, are hydrogen or $C_1$-$C_4$-alkyl;

X is methine, with the provisos, a) A is not —C≡N, when $R^4$ and/or $R^5$ are methyl or benzyl, and b) $R^1$ is not ethyl, when $R^4$ is hydrogen and $R^5$ is benzyl, as well as its alkali metal, alkaline earth metal, ammonium and organic ammonium salts, and their optically active isomers.

3. A derivative according to claim 1 in which $R^1$ is hydrogen, $C_1$-$C_{12}$-alkyl optionally substituted by di-$C_1$-$C_4$-alkylmethylenimino or di-$C_1$-$C_4$-alkylmethylenimino.

4. A derivative according to claim 3 in which and any alkyl group in $R^1$ contains 1 or 2 carbon atoms.

5. A derivative according to claim 1 in which $R^1$ is hydrogen, methyl, ethyl, dimethylmethylenimino or —(CH$_2$)$_2$ON=C(CH$_3$)$_2$ and $R^5$ is ethyl, propyl, isopropyl, CH(CH$_3$)CH$_2$CH$_3$ or cyclohexyl.

6. A derivative according to claim 5 in which $R^1$ is hydrogen.

7. A herbicidal composition according to claim 1, in which $R^2$ and $R^3$ are $C_{1-4}$ alkoxy, $R^4$ is hydrogen and A is —CO—OR$^1$.

8. A herbicidal composition according to claim 7, in which $R^1$ is hydrogen, $C_{1-12}$-alkyl optionally substituted by di-$C_1$-$C_4$-alkylmethylenimino or di-$C_1$-$C_4$-alkylmethylenimino and $R^5$ is $C_1$-$C_{10}$-alkyl or $C_3$-$C_8$-cycloalkyl.

9. A herbicidal composition according to claim 8, in which $R^2$ and $R^3$ are methoxy and any alkyl group in $R^1$ contains 1 or 2 carbon atoms and $R^5$ contains 2 to 6 carbon atoms.

10. A herbicidal composition according to claim 9, in which $R^1$ is hydrogen, methyl, ethyl, dimethylenimino or —(CH$_2$)$_2$ON=C(CH$_3$)$_2$ and $R^5$ is ethyl, propyl, isopropyl, CH(CH$_3$)CH$_2$CH$_3$ or cyclohexyl.

11. A herbicidal composition according to claim 10, in which $R^1$ is hydrogen an $R^5$ is isopropyl.

12. A method of combating weeds which comprises applying to the weeds or their locus a herbicidally effective amount of a compound according to claim 2 in which $R^2$ and $R^3$ are $C_{1-4}$alkoxy, $R^4$ is hydrogen and A is —CO—OR$^1$.

13. A method of combating weeds which comprises applying to the weeds or their locus a herbicidally effective amount of a compound according to claim 12 in which $R^1$ is hydrogen, $C_{1-12}$alkyl optionally substituted by di-$C_1$-$C_4$-alkylmethylenimino or di-$C_1$-$C_4$-alkylmethylenimino and $R^5$ is $C_1$-$C_{10}$-alkyl or $C_3$-$C_8$-cycloalkyl.

14. A method of combating weeds which comprises applying to the weeds or their locus a herbicidally effective amount of a compound according to claim 13 in which $R^2$ and $R^3$ are methoxy and any alkyl group in $R^1$ contains 1 or 2 carbon atoms and $R^5$ contains 2 to 6 carbon atoms.

15. A method of combating weeds which comprises applying to the weeds or their locus a herbicidally effective amount of a compound according to claim 14 in which $R^1$ is hydrogen, methyl, ethyl, dimethylenimino or —(CH$_2$)$_2$ON=C(CH$_3$)$_2$ and $R^5$ is ethyl, propyl, isopropyl, (CH(CH$_3$)CH$_2$CH$_3$ or cyclohexyl.

16. A method of combating weeds which comprises applying to the weeds or their locus a herbicidally effective amount of a compound according to claim 15 in which $R^1$ is hydrogen and $R^5$ is isopropyl.

17. Substituted 2-pyrimidinyl acetic acid derivative of the formula

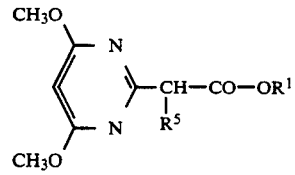

in which $R^1$ is hydrogen, $C_1$-$C_{12}$-alkyl (optionally substituted by hydroxy, halogen, $C_1$-$C_4$-alkoxy, $C_1$-$C_4$-alkylthio, $C_3$-$C_6$-cycloalkyl, benzyl, furyl, tetrahydrofuryl, phenyl, halophenyl, $C_1$-$C_4$-alkylphenyl, $C_1$-$C_4$-alkoxyphenyl, nitrophenyl, cyano, carboxy, $C_1$-$C_4$-alkoxycarbonyl, $C_1$-$C_4$-alkylamino, di-$C_1$-$C_4$-alkylamino, tri-$C_1$-$C_4$-alkylammoniumhalide, $C_2$-$C_5$-alkylenimino or di-$C_1$-$C_4$-alkylmethyleniminooxy), $C_2$-$C_{12}$-alkyl, interrupted by one or more oxygen or sulphur atoms and optionally substituted by hydroxy, halogen, $C_1$-$C_4$-alkoxy, $C_1$-$C_4$-alkylthio, $C_3$-$C_6$-cycloalkyl, benzyl, furyl, tetrahydrofuryl, phenyl, halophenyl, $C_1$-$C_4$-alkylphenyl, $C_1$-$C_4$-alkoxyphenyl, nitrophenyl, cyano, carboxy, $C_1$-$C_4$-alkoxycarbonyl, $C_1$-$C_4$-alkylamino or di-$C_1$-$C_4$-alkylamino, a $C_3$-$C_8$-alkenyl or $C_3$-$C_8$-alkynyl group (each of which is optionally substituted by $C_3$-$C_8$-alkoxy, phenyl or halogen), $C_3$-$C_8$-cycloalkyl, optionally substituted by methyl, di-$C_1$-$C_4$-alkylmethylenimino or $C_3$-$C_6$-cycloalkylenimino;

$R^5$ is isopropyl, and its alkaline metal, alkaline earth metal, ammonium and organic ammonium salts and the optically active isomers thereof.

* * * * *